United States Patent [19]

Loos et al.

[11] Patent Number: 5,728,076

[45] Date of Patent: Mar. 17, 1998

[54] AMPOULE HOLDER AND ACTUATOR

[75] Inventors: Hans Joachim Loos, Ginsheim-Gustavsburg; Günter Ziegert, Frankfurt am Main, both of Germany

[73] Assignee: Hoechst Aktiengesellschaft, Frankfurt am Main, Germany

[21] Appl. No.: 847,603

[22] Filed: Apr. 25, 1997

Related U.S. Application Data

[63] Continuation of Ser. No. 232,348, Apr. 22, 1994, abandoned, and a continuation of Ser. No. 743,788, Aug. 12, 1991, abandoned.

[30] Foreign Application Priority Data

Aug. 14, 1990 [DE] Germany .................. 40 25 717.7

[51] Int. Cl.$^6$ .................................................. A61M 5/00
[52] U.S. Cl. ................................... 604/232; 604/228
[58] Field of Search ........................... 604/232–234, 604/187, 218, 403, 411, 415, 175, 227, 228, 240, 201; 222/326, 327

[56] References Cited

U.S. PATENT DOCUMENTS

| | | | |
|---|---|---|---|
| 1,604,018 | 10/1926 | Brockway | 604/233 |
| 1,728,260 | 9/1929 | Marcy | 604/232 |
| 1,782,938 | 11/1930 | Pletcher | 604/232 |
| 2,147,616 | 7/1939 | Chaput | 604/232 |
| 2,678,647 | 5/1954 | Bruger | 604/227 |
| 2,986,141 | 5/1961 | Hart . | |
| 3,026,873 | 3/1962 | Miskel et al. | 604/232 |
| 3,076,455 | 2/1963 | McConnaughey et al. | 604/232 |
| 3,108,592 | 10/1963 | Hassing et al. | 604/232 |
| 3,144,178 | 8/1964 | Sarnoff . | |
| 3,811,441 | 5/1974 | Sarnoff | 604/234 |
| 4,281,653 | 8/1981 | Barta et al. . | |
| 4,585,445 | 4/1986 | Hadtke | 604/234 |
| 4,643,724 | 2/1987 | Jobe | 604/232 |
| 4,687,472 | 8/1987 | Gross | 604/227 |
| 4,723,945 | 2/1988 | Theiling | 604/232 |
| 4,931,040 | 6/1990 | Haber et al. | 604/232 |
| 4,944,723 | 7/1990 | Haber et al. . | |

FOREIGN PATENT DOCUMENTS

| | | | |
|---|---|---|---|
| 0102221 | 10/1937 | Australia | 604/227 |
| 0100369 | 2/1984 | European Pat. Off. . | |
| 1 161 049 | 8/1958 | France . | |
| 835 780 | 4/1952 | Germany . | |
| 1 035 325 | 9/1954 | Germany . | |
| 1 086 013 | 3/1957 | Germany . | |
| 29 15 338 A1 | 10/1980 | Germany . | |

OTHER PUBLICATIONS

European Search Report with English translation.

*Primary Examiner*—Mark Bockelman
*Attorney, Agent, or Firm*—Finnegan, Henderson, Farabow, Garrett & Dunner, L.L.P.

[57] ABSTRACT

A holder for cylindrical ampoules includes a receiving device provided for receiving the cylindrical ampoule and a handle with a bore for receiving a longitudinally displaceable piston rod with an actuating device, the receiving device is integrally formed with the handle and includes a collar with an allround groove in its root.

5 Claims, 1 Drawing Sheet

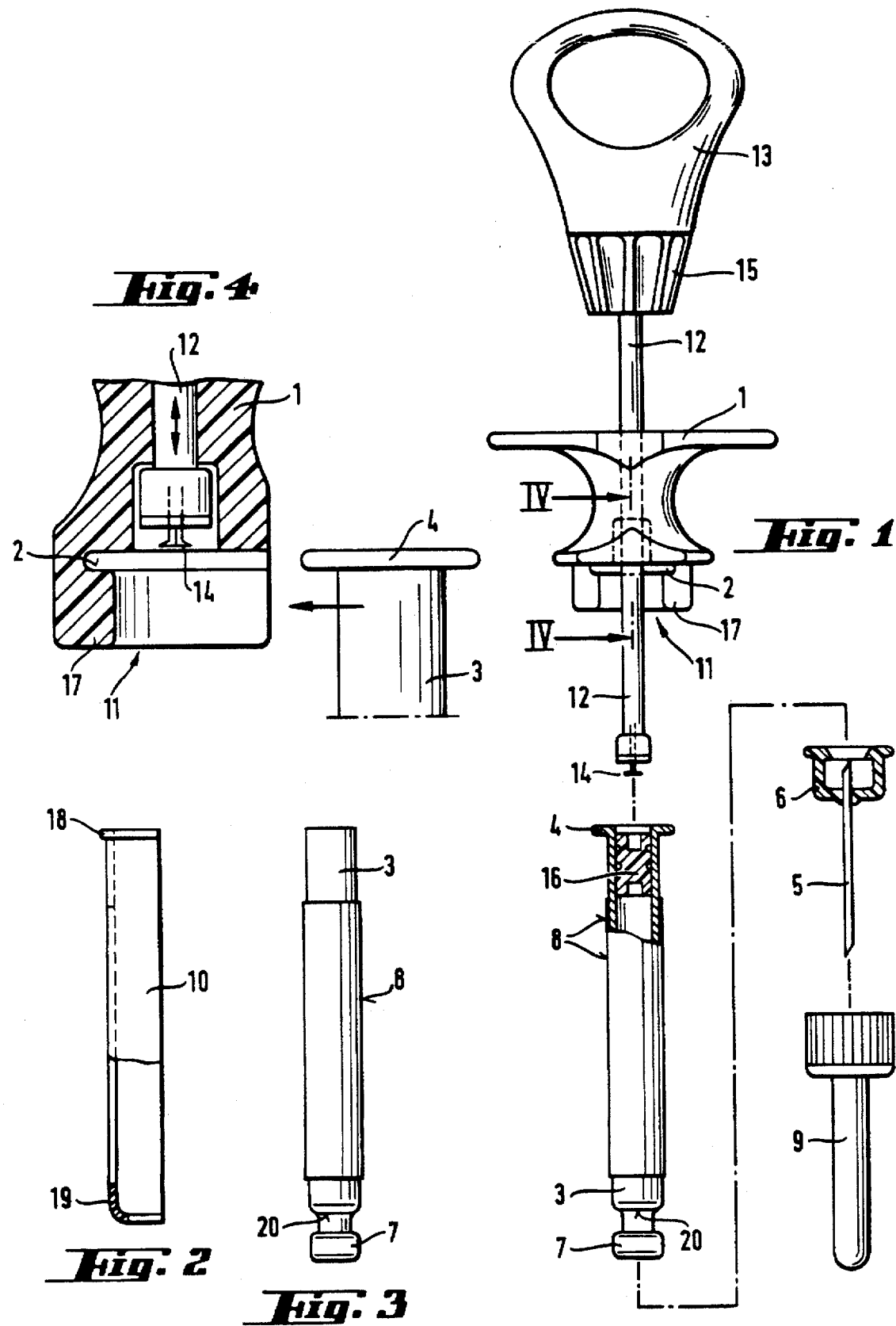

AMPOULE HOLDER AND ACTUATOR

This is a continuation of application Ser. No. 08/232,348, filed Apr. 22, 1994, now abandoned, and a continuation of application Ser. No. 07/743,788, filed Aug. 12, 1991, now abandoned.

BACKGROUND OF THE INVENTION

1. Field of the Invention

The invention relates to a syringe holder for cylindrical ampoules, having a receiving device for receiving the cylindrical ampoules and a handle with a bore for receiving a longitudinally displaceable piston rod with an actuating device.

2. Description of the Related Art

Syringe holders of the said type have been disclosed by German Patent 2,915,338 and comprise holding the ampoule in a sleeve, which can receive a cannula at its front end and, at its rear end, has a handle with bores, which is intended to receive a piston rod provided with an actuating device. The ampoule is closed at one end by a stopper which acts as a piston and in which the piston rod engages, and by a rubber membrane with a metal cap at the other end. This syringe holder is expensive in manufacture, operation and maintenance.

SUMMARY OF THE INVENTION

This is to be remedied by the invention. The invention as described in the claims achieves the object in such a way that the receiving device for the ampoule comprises a U-shaped collar with an allround groove in its root.

To receive cylindrical ampoules without a flange at the end closed by the stopper, the collar with an allroundgroove can have an adaptor which is formed as a U-shaped channel which is provided with a flange at one end and with a cap at the other end.

The advantages of the invention are essentially to be seen in easier operation and maintenance (no autoclaving of the syringe holder).

BRIEF DESCRIPTION OF THE DRAWINGS

The invention is explained in more detail below by reference to drawings which show merely one possible embodiment and in which FIG. 1 shows the syringe holder with a cylindrical ampoule and a disposable cannula with a protective cap, in accordance with the invention;

FIG. 2 shows an adaptor of the invention in partial section;

FIG. 3 shows a cylindrical ampoule of the invention without flange; and

FIG. 4 shows an enlarged partial section taken along the line IV—IV in FIG. 1.

DESCRIPTION OF THE PREFERRED EMBODIMENT

The receiving device 11, provided in the syringe holder is an integral part of the handle 1 which is provided with a bore for receiving a longitudinally displaceable piston rod 12 with an actuating device 13. In the piston rod 12, claws 14 are provided which are handled by means of the manipulator 15. By means of the claws 14, the piston rod can be positively joined to the stopper 16 which acts as the piston and which positively holds the ampoule 3. The receiving device 11 for the ampoule 3 comprises a U-shaped collar 17 with an allround groove 2 in its root. The opening of the collar 17 corresponds to the diameter of the ampoule 3, whose allround flange 4 engages in the groove 2.

For ampoules without a flange, an adaptor 10, which is formed as a channel of U-shaped cross-section with a flange 18 and a cap 19, is provided for the receiving device 11. The ampoule 3 is supported by its shoulder 20 in the cap 19. 8 indicates a film label acting as a splinter guard. The locking cap 6 with the cannula 5 is slipped over the film head 7 which engages behind the ampoule head 7. The cannula 5 is provided with a protective cap 9. The piston rod 12 can additionally be fitted with a metering scale and a metering adjustment device (not shown).

The syringe holder can be used both for cylindrical ampoules and for disposable syringes. The syringe holder is suitable for injections of any type, and also for taking blood samples and for emptying paste and ointment cartridges.

What is claimed is:

1. A holder for an ampoule having an upper opening enclosed by a movable stopper and a lower opening through which fluid is injected, comprising:
   a handle having a central bore extending therethrough;
   a U-shaped collar attached to and extending from the handle for selectively supporting the ampoule, the collar defining a recess coaxial with the bore and a lateral opening through which an upper portion of the ampoule is inserted to be supported within the recess, the collar further including an internal groove;
   an actuator including a displaceable piston rod extending through the bore for engaging the stopper of the ampoule to inject fluid through the lower opening; and
   an adaptor for engaging the ampoule with the collar, the adaptor including a first end having a flange receivable in the groove and a second end having a cap portion for receiving the ampoule.

2. An apparatus, comprising:
   a handle having a piston bore extending therethrough;
   a displaceable piston rod extending through the piston bore, and having a first end and a second end;
   an actuator located on the first end of the piston rod;
   a claw located on the second end of the piston rod;
   receiving means, located in the handle, for engaging and selectively holding an ampoule, the receiving means including a U-shaped collar defining a recess coaxial with the piston bore and a lateral opening through which an upper portion of the ampoule is inserted to be supported within the recess, the collar further including an internal groove adjacent an end of the piston bore and extending about an edge of the collar;
   an ampoule having a first end and a second end, the second end of the ampoule having a head; and
   an adaptor having first and second ends, the first end of the adaptor including a flange shaped to be received by the groove, and the second end of the adaptor having a cap portion for receiving the ampoule.

3. An apparatus as claimed in claim 2, further including a locking cap adapted to fit on the head, the locking cap having a cannula extending therefrom.

4. An apparatus as claimed in claim 2, wherein the ampoule includes a stopper located therein, the stopper having an opening for receiving the claw.

5. An apparatus as claimed in claim 2, wherein the bore of the receiving means is substantially cylindrical.

* * * * *